Figure 1:
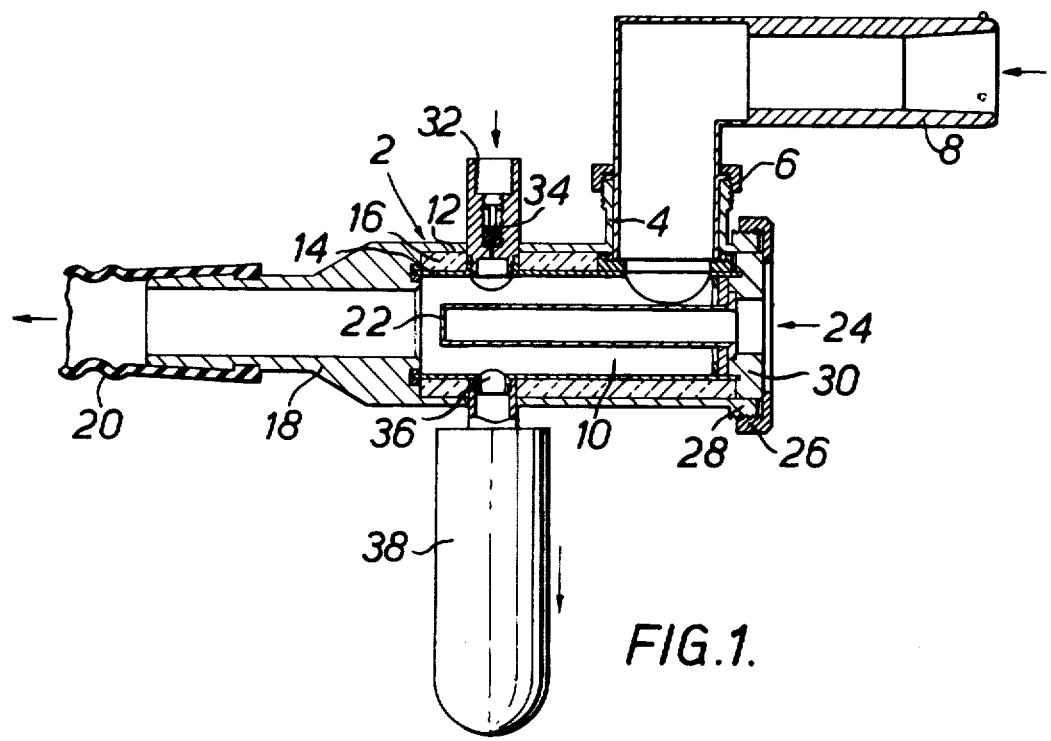

United States Patent [19]

Fodor

[11] 4,038,980

[45] Aug. 2, 1977

[54] AIR HUMIDIFIERS

[76] Inventor: Imre Fodor, 7 Hernes Close, Hernes Road, Oxford, England

[21] Appl. No.: 522,100

[22] Filed: Nov. 8, 1974

[30] Foreign Application Priority Data

Nov. 12, 1973 United Kingdom ............ 52495/73

[51] Int. Cl.² .......................................... A61M 16/00
[52] U.S. Cl. .................................... 128/193; 261/130
[58] Field of Search ............ 128/193, 194, 192, 212, 128/188, 214 C, 256, 368, 400, 402, 142, 142.3, 145.5, 145.6, 145.8; 261/130, 131, 142

[56] References Cited

U.S. PATENT DOCUMENTS

| 1,421,756 | 7/1922 | Arnao ................................ 128/368 |
| 1,554,219 | 9/1925 | Kitchen .............................. 128/193 |
| 2,902,269 | 9/1959 | Eichelman .......................... 128/186 |
| 3,215,416 | 11/1965 | Liben .................................. 261/142 |
| 3,291,122 | 12/1966 | Engstrom et al. .................. 128/194 |
| 3,434,471 | 3/1969 | Liston ................................. 128/192 |
| 3,454,005 | 7/1969 | Eubanks et al. ................... 128/186 |
| 3,695,267 | 10/1972 | Hirtz et al. ......................... 128/192 |
| 3,864,544 | 2/1975 | Amerongen ....................... 128/193 |

Primary Examiner—Robert W. Michell
Assistant Examiner—Henry J. Recla
Attorney, Agent, or Firm—Bacon & Thomas

[57] ABSTRACT

An air humidifier for a surgical breathing machine has an evaporating chamber containing a temperature regulated low thermal mass heater. A water drip feed unit drips water onto a sheath of porous material of the heater at a predetermined rate. The water is substantially completely and instantaneously evaporated in the manner of a flash boiler to create an air temperature and relative humidity within predetermined limits. The heater temperature and water supply rate have manual adjustment means coupled together so that the predetermined limits are not exceeded. The evaporating chamber is tubular and of similar cross section to interconnecting conduits so as not unduly to interfere with pressure waves from the breathing machine.

11 Claims, 2 Drawing Figures

AIR HUMIDIFIERS

This invention relates to air humidifiers for surgical or veterinary purposes, particularly though not exclusively for use with breathing machines.

A known air humidifier for a surgical breathing machine comprises a large e.g. 4 liter reservoir of water warmed by a thermostatically controlled ¾ kilowatt heater to about 40°C. The humidifier is connected between the breathing machine and the patient so that air from the machine is passed over the surface of the water to attain the desired humidity and temperature.

It is important that air from such breathing machines be kept within strictly defined limits of pressure, flowrate humidity and temperature and in particular that the air humidifier be controllable so that the air temperature and humidity is kept within such limits. Difficulties have arisen in controlling the temperature and vapourisation of the water of this known humidifier by reason of its large thermal mass and its consequent slowness in reacting to control signals.

A further serious disadvantage of the known humidifier is that the reservoir of water at 40°C. provides good conditions for bacterial growth, which may put at risk the sterile conditions required. If however the temperature of the water were to be raised to prevent bacterial growth, there would be a risk of delivering air to the patient at an excessive temperature.

Another disadvantage of the known humidifier is that its large volume considerably dampens the pressure waves required to be produced by the breathing machine for the purpose of inflating the patient'lungs.

It is an object of the invention to provide a simple and inexpensive air humidifier.

It is another object of the invention to provide an air humidifier which is accurately controllable to provide an air temperature and relative humidity within predetermined limits and which provides humidified air in a sterile condition.

It is a further object of the invention to provide an air humidifer which does not interfere to any substantial extent with pressure waves passing therethrough generated by a breathing machine.

The present invention provides an air humidifier having an air inlet and air outlet communicating with each other by way of an evaporating chamber in which is disposed a heater, means being provided for directing a supply of water into said chamber and into heat exchange relationship with the heater at a predetermined rate, the supply rate being such in relation to the heater that in use substantially complete and instantaneous evaporation of the water occurs in the manner of a flash boiler to create an accurately controllable air temperature and relative humidity within the limits defined herein.

In regard to the "limits" referred to above, where the air humidifier is required for surgical purposes, it must be able to keep the air temperature within the limits of 32° to 38° C as measured close to the point of delivery of air to the patient. A higher temperature would result in tissue damage to the breathing organs, and a lower temperature would result in insufficient humidification. The humidity should be kept within the limits of 65 to 85% R.H. at 36° C and at atmospheric pressure. These limits must be maintained at flow-rates between 1 litre of air per minute (for a small baby to 30 liters of air per minute (for a large adult) and pressures between 50 cm water gauge above atmospheric pressure and atmospheric pressure.

Where the air humidifier is required for veterinary purposes, it may be necessary to alter the above defined limits, depending on the particular animal to be treated. Such limits will be well known to those skilled in the veterinary arts.

In use of a humidifier according to the invention a controlled quantity of water is rapidly boiled. The air humidity is determined by the amount of water boiled by the heater, which can be accurately controlled by adjusting the water supply rate. The air temperature is a function of heat transfer directly from the heater to passing air and also of the amount of water evaporated by the heater. The air temperature may therefore be accurately controlled by adjusting the water supply rate. Alternatively or in addition the air temperature may be controlled by adjusting the heater temperature. Since the heater does not have to warm a large amount of water, in contrast to the above described known humidifier, the heater can have a very low thermal mass (20g. of copper alloy has proved sufficient) and there will be therefore a rapid and accurate response of the heater to temperature control signals.

Any suitable means may be employed for controlling the temperature of the heater; it may be thermostatically controlled by temperature sensing means disposed adjacent a patient to whom the air passing through the humidifier is being supplied or and as preferred for simplicity by temperature sensing means integral with the heater element.

As a safegaurd against too high a temperature of humidified air being reached as a result of settings of water supply rate or heater temperature, it is advantageous to couple the controls for water supply rate and heater temperature so that the heater temperature always bears a predetermined relation to the water supply rate whereby an excessive temperature is not reached. Such coupling may be effected by any suitable means for example by a mechanical linkage.

Whilst control means may be provided automatically to regulate the water supply rate in response to means sensing the relative humidity, it is preferred from the point of view of simplicity to provide a manual control of the water supply rate, and the manual control to be adjusted with the aid of a suitable metering arrangement of the water supply rate.

The water supply directing means may be in the form of a nozzle or spout for emitting a fine spray of water under pressure and directing it onto the heater. Such a fine spray has the advantage that the heater easily evaporates the small droplets. Alternatively and as preferred for simplicity the directing means comprises a fine bore tube for supplying water in the form of drops to the heater.

The water supply directing means may be arranged to direct water directly onto the surface of the heater; where however the water is supplied in the form of drops, it is preferred to interpose on the surface of the heater absorbent material for absorbing the water and ensuring a good heat transfer to the water.

A water receptacle is preferably dispose below the heater in case the heater fails, so that water entering the humidifier is trapped in the receptacle and there is no risk of the water finding its way to the air outlet and to the patient.

Where the humidifier is to be used with a breathing machine, it is preferably such as not to interfere to any substantial extent with the required values of air pressure (be it a constant pressure or pressure waves for inflating the patients lungs) and air flow rate as set by the controls of the breathing machine, so that it is not necessary to compensate in the breathing machine controls for the presence of the air humidifier.

Now since the heater of the humidifier of the present invention can have a low thermal mass, it may be small in size and may be disposed in an evaporating chamber of small volume. An evaporating chamber of small volume has the advantage that pressure waves from a breathing machine passing through the chamber are not dampened to any serious extent. For clinical purposes, an acceptable volume of the chamber would be no greater than 200 cm$^3$. There should also be in the humidifier no more than 2 cm water resistance to flow at a flow rate of 30 liters per minutes.

The present invention therefore extends to an air humidifier as defined above for use with a breathing machine and having an evaporating chamber of sufficient small volume and being such that there is in use no substantial interference with air flow and air pressure as determined by the breathing machine.

Figure 2:
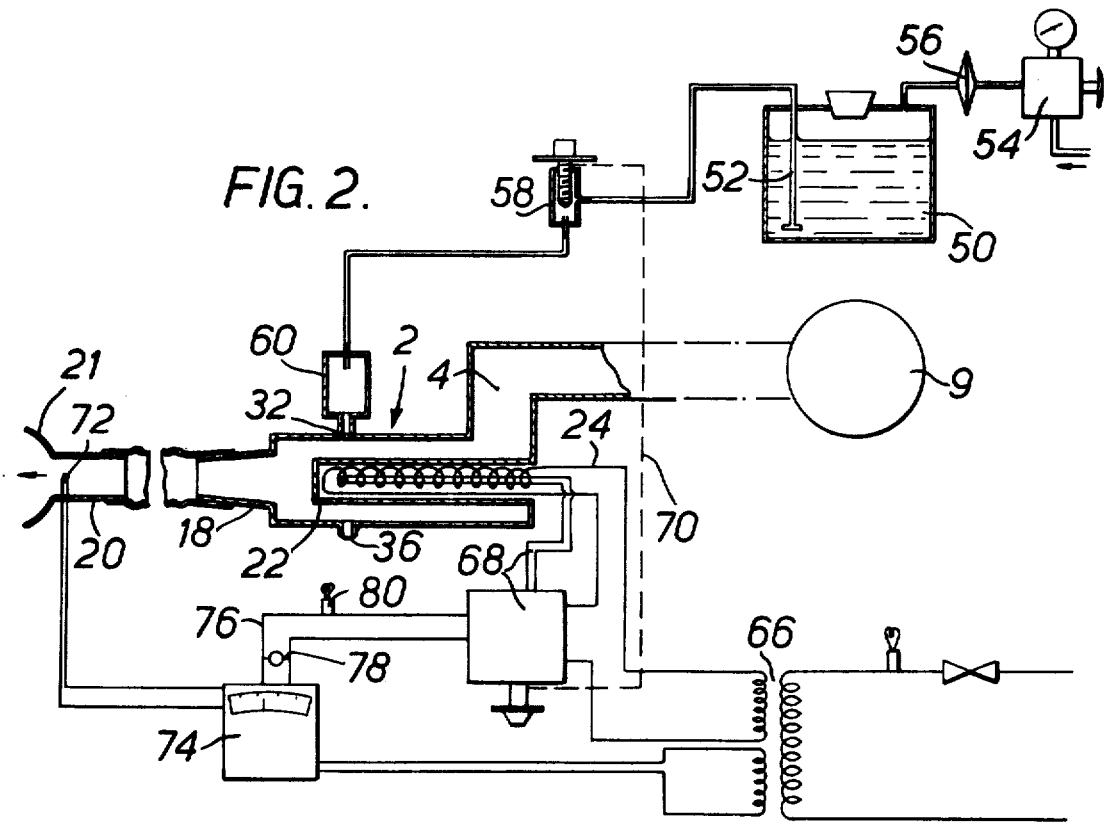

A preferred embodiment of the invention will now be described with reference to the accompanying drawing, wherein:

FIG. 1 is a side sectional view of an air humidifier according to the invention; and FIG. 2 is a diagram of a control circuit for the humidifier of FIG. 1.

Referred to FIG. 1, the air humidifier has a tubular body 2 having in its side adjacent one end on air inlet port 4. Port 4 is threaded to receive a locking ring 6 for securing an inlet pipe 8. Pipe 8 is connected to a source of air 9 e.g. a breathing machine.

Inlet port 4 communicates with an evaporating chamber 10. Chamber 10 is surrounded by cavity walls 12, 14 having thermal insulation 16 therebetween. The evaporating chamber 10 communicates with a tubular air outlet port 18 having a tapering outer surface formed to be inserted in a flexible thermally insulated hose 20, which conducts air from chamber 10 to a mask 21 for the patient's mouth.

Chamber 10 contains a centrally disposed sheath 22 of stainless steel woven wire. A heating element 24 (not shown in FIG. 1 but see FIG. 2) of low thermal mass, about 20° g Cu, is inserted into sheath 22. A locking ring 26 screwed onto an annular boss 28 at the end of chamber 10 and a washer 30 serve to releasably secure element 24, sheath 22 and wall 14 in chamber 10.

At the end of sheath 22 adjacent outlet port 18 is disposed a water drip feed unit inlet comprising a tubular insert 32 having internal elements 34 with bores of predetermined diameter to regulate the rate of feed of water drops onto sheath 22.

An outlet 36 immediately below insert 32 serves to conduct any excess water from chamber 10 into a transparent removable container 38.

Referring now to the control circuit of FIG. 2 the water supply for the drip feed comprises a reservoir 50 having an outlet pipe 52 through which water is forced by pressurising the reservoir from a compressed air supply. The compressed air passes through an adjustable pressure regulator 54 and a bacterial filter 56. The water flow from reservoir 50 is regulated by a manually adjustable needle control valve 58. Water from valve 58 gathers in the bottom of an inspection chamber 60 before passing into evaporating chamber 10 via insert 32.

Heating element 24 is powered by a 6.V. A.C. supply derived from a mains transformer 66. Element 24 is powered via a manually adjustable thermostat arrangement indicated at 68. The manual adjustments for thermostat 68 and valve 58 are mechanically coupled by a gearing arrangement indicated schematically as at 70.

A temperature sensing thermocouple 72 is disposed in hose 20 adjacent the patient's mask 21. The voltage from the thermocouple is amplified and indicated in terms of temperature in a unit 74. Unit 74 also has a non-resetting thermal cutout for sensing an excess temperature and for providing an alarm signal on lines 76 to thermostat 68 to switch off power to element 24. A sonic alarm 78 and a visual alarm 80 are connected to lines 76. Unit 74 is powered from transformer 66.

The entire control circuit may be provided as a single unit in a container with suitable connections to the humidifier, mains power supply and a source of compressed air.

In operation of the humidifier, the air flowing through the inlet 4 of the humidifier is first warmed by direct heat transfer from sheath 22. The air then flows into the region adjacent the outlet where water is evaporating on sheath 22.

The surface of the sheath 22 is kept considerably above the boiling point of water typically 200°-300°C so that a drop of water falling on to it will be vaporised substantially instantaneously and completely in the manner of a flash boiler. Bacterial growth is thus prevented. If the heater had no sheath but a plain metal surface, a drop of water falling on to it may become "spheroidal," a physical condition in which water vapour reduces heat flow to the liquid water and slows vaporisation. The surface of the heater is therefore covered by porous sheath 22. Whilst sheath 22 is preferably formed of steel wire, it may alternatively be formed of mineral fibre or porous ceramic.

By controlling the flow of water and temperature of sheath 22 by thermostat 68 and valve 58, it is possible to determine exactly the resultant degree of humidity in the air flow through the humidifier and to produce optimal humidity in a known air flow. The water flow required is about 0.04 cc per litre of air per minute. Valve 58 may conveniently be calibrated in terms of litres of air per minute to simplify the control of humidity. It has been found most convenient to control the temperature of sheath 22 by means of thermostat 68 coupled to the heater rather than by a remote sensor in the air flow path. The small thermal mass of the humidifier makes it possible to provide accurate thermostatic temperature control of the heater and thus of the inspired air. An advantage of the invention is that the outlet temperature is to some extent self-regulating. Heat transfer from the sheath to dry air flow is not efficient and it has been found, if no water is supplied, the air temperature at the delivery point to the patient is lower than that obtained with optimal water supply, and that if the water supply is increased above optimal, the delivered temperature is again reduced.

The humidified and heated air flows through the outlet 18 to the patient. As a result of the tubular configuration of evaporating chamber 10 being generally similar of that of the inlet and outlet pipe 8, 20 there is little resistance or damping of pressure waves passing through the chamber from a breathing machine.

If, through any malfunction water air is delivered to the patient at an excess temperature thermocouple 72 detects the excess temperature to shut down heater 24.

In normal conditions, thermocouple 72 monitors the air temperature and this is displayed by unit 74.

If through any malfunction water is not evaporated in chamber 10 but flows through outlet 36 into transparent container 38, the presence of water in the container will warn nursing staff of humidifier failure. The transparent container 38 should preferably have a volume adequate to collect the volume of water stored in reservoir 50, or may be automatically self-emptying if fitted with a float operated valve.

Another means of dispensing water to the humidifier is to use a gravity operated drip feed unit with a calibrated jet and control valve, such as it used medically for giving intravenous fluids. With this type of dispenser it is normal to count the number of drops per minute and convert this figure to a volume rate using information provided by the manufacturer. It would be necessary to adjust the flow rate of water manually to suit the flow rate of air through the humidifier being used to ventilate the patient.

Whilst the preferred embodiment has been described as applied in a breathing machine, many other applications of the humidifier according to the invention are possible. For example a patient with a tracheotomy may be supplied with the humidifier since the air he breathes may not otherwise be sufficiently humid, as the nose, which normally humidifiers air for breathing, is by-passed. Laboratory experiments may also require an atomosphere of a predetermined temperature and humidity, and the humidifier may be useful in such experiments.

Whilst a preferred embodiment has been described, it will be understood that various modifications and substitutions may be made to the preferred embodiment without departing from the invention which is limited only by the appended claims.

What is claimed is:

1. A surgical breathing machine incorporation an air humidifier, said machine including an air flow generator and conduit means connecting said generator to said humidifier, said humidifier comprising a body member defining an air heating and water evaporating chamber, an air inlet to said chamber an and an air outlet from said chamber provided in said body member, said air inlet being in communication with said conduit means, a heater disposed in said chamber, means for adjusting the temperature of the heater, a source of water, water inlet means in said body member for directing a supply of water from said source into said chamber and towards said heater, a member of porous material disposed adjacent said heater, whereby to intercept said water supply and bring water into a heat exchange relationship with said heater, means for adjusting the rate of supply of water from said water source to said water inlet means, and coupling means coupling said temperature adjusting means supply rate adjusting means so that one adjusting means is varied when the other adjusting means is varied, whereby in operation regulation of the heater temperature and water supply rate can be obtained to cause substantially complete and instantaneous evaporation of the water by the heater in the manner of a flash boiler, the vaporized water passing into the air flowing through and heated within the chamber to create an air temperature and relative humidity within predetermined limits.

2. The combination of claim 1, wherein said water supply rate adjusting means comprises a manually adjustable needle valve.

3. The combination of claim 1 wherein said water source comprises a water container, the container having an air inlet and a water outlet and including a source of air connected to said air inlet for pressurizing the container to force the water through said water outlet, said water outlet communicating with said water inlet in the body member.

4. The combination of claim 1 wherein said air inlet and air outlet are disposed in spaced apart relationship, and said water inlet means is disposed intermediate said air inlet and air outlet, and said heater extends between said air inlet and said water inlet means so that air from the air inlet passes over at least a portion of the heater before reaching a zone in which evaporation takes place.

5. The combination of claim 1 wherein the temperature adjusting means includes a thermostat control arranged to sense the temperature of said heater and connected to control the supply of power to said heater.

6. The combination of claim 1 wherein said evaporating chamber is tubular with said air inlet and outlet at opposite ends of the tubular chamber.

7. The combination of claim 6 wherein the cross-sectional size of the chamber is generally the same as said air inlet and outlet.

8. The combination of claim 6 wherein said heater extends centrally within said chamber between said air inlet and said air outlet.

9. The combination of claim 8 wherein said water inlet means is disposed adjacent the end of the chamber including the air outlet.

10. The combination of claim 8 wherein said member of porous material adjacent said heater is a tubular sheath of porous material surrounding the heater.

11. The combination of claim 1 wherein the evaporating chamber is a hollow cavity having internal walls provided with thermal insulation thereon.

* * * * *